US005800562A

United States Patent [19]
Wilkinson

[11] Patent Number: 5,800,562
[45] Date of Patent: Sep. 1, 1998

[54] PROSTHETIC APPARATUS FOR ABSORBING SHOCKS

[76] Inventor: Kerry E. Wilkinson, 5750 W. Linda La., Chandler, Ariz. 85226

[21] Appl. No.: 929,009

[22] Filed: Sep. 8, 1997

[51] Int. Cl.$^6$ ........................................... A61F 2/60
[52] U.S. Cl. ................................. 623/27; 623/52
[58] Field of Search .................. 623/27, 35, 38, 623/50–52; 267/30, 140.4, 141 (U.S. only), 154 (U.S. only), 276, 283

[56] References Cited

U.S. PATENT DOCUMENTS

| | | | |
|---|---|---|---|
| 622,140 | 3/1899 | Ginn | 623/35 |
| 1,783,801 | 12/1930 | Leipert | 267/30 |
| 5,211,667 | 5/1993 | Danforth | 623/35 |
| 5,702,488 | 12/1997 | Wood et al. | 623/27 |

*Primary Examiner*—David H. Willse
*Attorney, Agent, or Firm*—H. Gordon Shields

[57] ABSTRACT

Prosthetic shock absorber rotation apparatus for a prosthetic leg includes an outer cylindrical element which may be secured to a prosthetic foot and a tubular member which extends in the opposite direction and which may be secured appropriately at an attachment location above or below the knee. A sleeve is disposed in the two members and a bushing is secured to the tubular member and moves with the sleeve. Extending between the sleeve and the outer cylindrical element are elastomeric elements. The elastomeric elements are disposed within the sleeve and bear against a wall in the outer cylindrical element to absorb shocks. A spring element attached between the outer cylindrical element and the tubular member allows limited rotational flexibility.

7 Claims, 2 Drawing Sheets

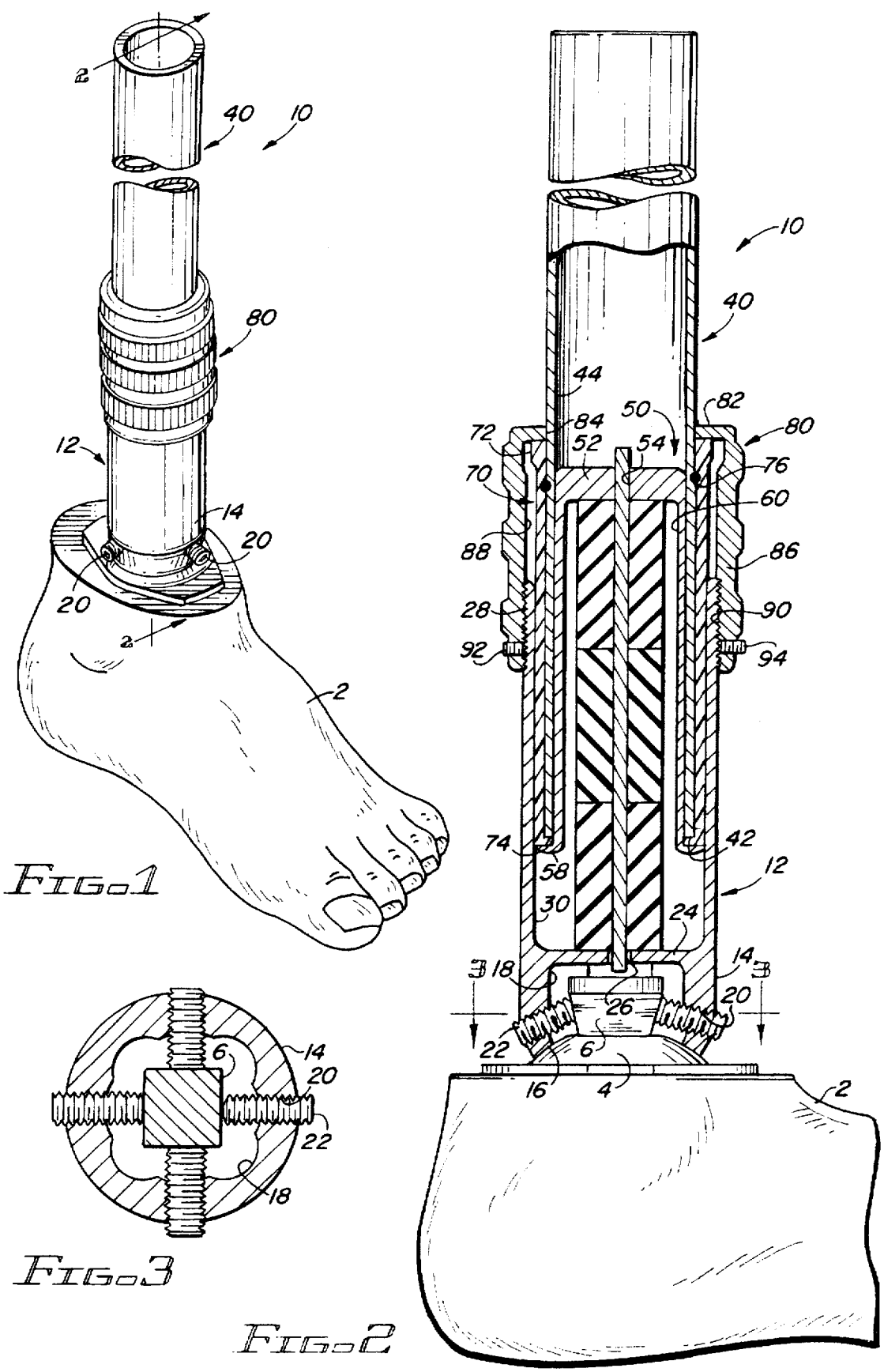

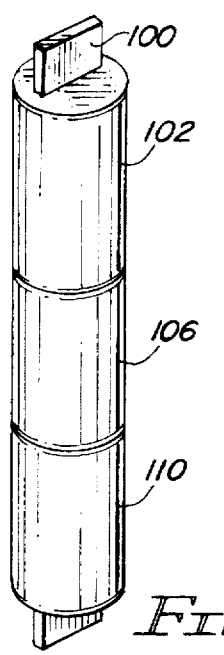
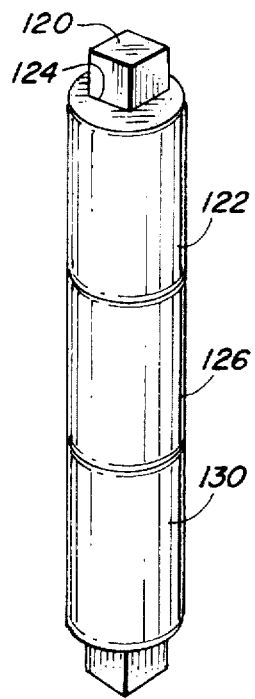
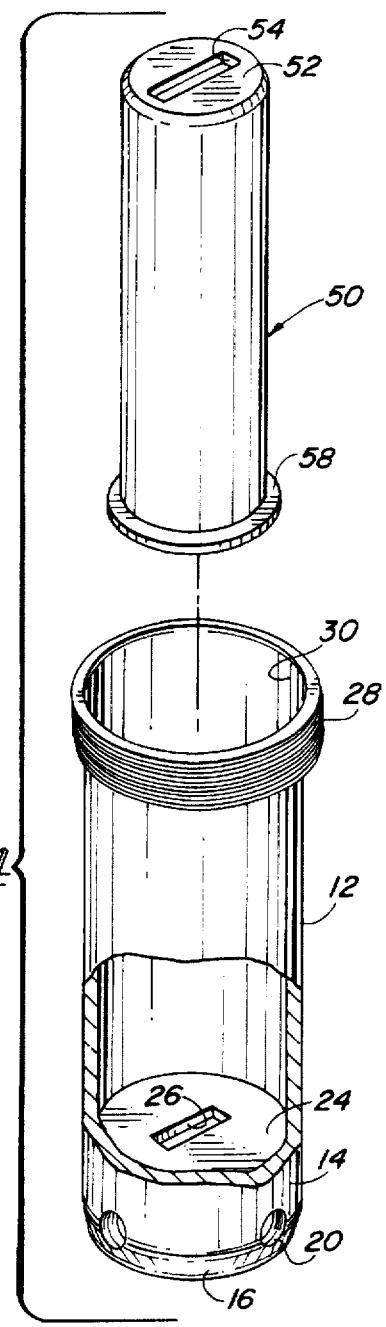
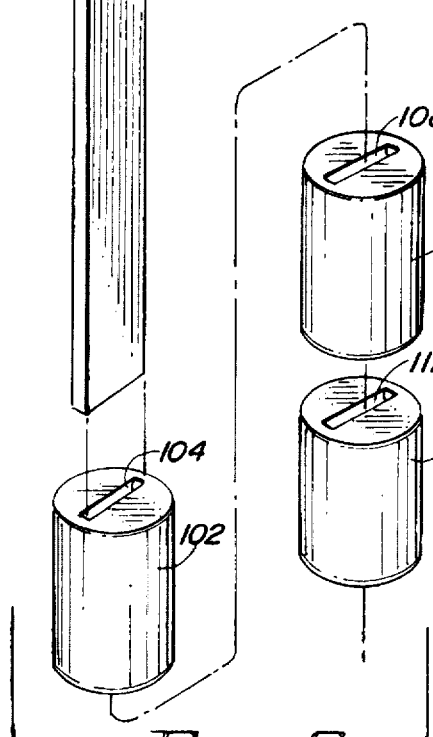
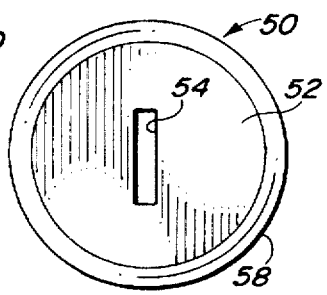
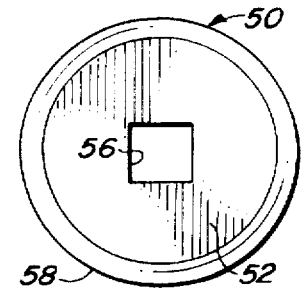

PROSTHETIC APPARATUS FOR ABSORBING SHOCKS

BACKGROUND OF THE INVENTION

1. Field of the Invention

This invention relates to a prosthetic apparatus, and, more particularly, to a shock absorber and rotation assembly for a prosthetic leg.

2. Description of the Prior Art

Two problems with prosthetic legs in general are the inability to absorb shocks and to rotate. Shock absorption increases the natural feel and comfort of the leg. Rotation to some degree allows a more ordinary turn while walking or even the pivot action required for golf, baseball, etc.

The apparatus of the present invention comprises a shock absorber which is efficient and light weight and provides a degree of rotational flexibility. The apparatus is made to interface with industry standard components and to fit anywhere between the foot and an upper socket or socket connector, as appropriate or as desired.

SUMMARY OF THE INVENTION

The invention claimed and described herein comprises a shock absorber assembly with limited axial rotation for a prosthetic leg. The apparatus includes an outer cylinder with a connector portion for connecting to another prosthetic element, and an inner cylinder movable relative to the outer cylinder. A bushing is disposed between the inner cylinder and the outer cylinder and the bushing is secured to the inner cylinder. A sleeve is in turn disposed within the inner cylinder and bears against the bushing. An elastomeric shock absorbing member extends between the outer cylinder and the sleeve, and a spring plate element is disposed within the elastomeric member and extends between the outer cylinder and the sleeve. The plate element provides a degree of rotational movement with the elastomeric element, and the elastomeric element provides the shock absorbing capabilities. If desired, the plate element may be replaced by a non-twisting element if no relative rotation between the outer cylinder and the inner cylinder is desired. The outer cylinder is adjustable axially relative to the inner cylinder by a threaded connection to the outer cylinder and may be locked in place by set screw elements.

Among the objects of the present invention are the following:

To provide new and useful prosthetic apparatus;

To provide new and useful prosthetic shock absorber apparatus;

To provide new and useful prosthetic apparatus with rotational capabilities;

To provide new and useful prosthetic shock absorber assembly having an inner sleeve and an outer sleeve and relative rotation between the two; and To provide new and useful shock absorber elements including an elastomeric element disposed between the outer cylinder and an inner cylinder through a sleeve and a bushing.

BRIEF DESCRIPTION OF THE DRAWING

FIG. 1 is a perspective view of the apparatus of the present invention in the use environment secured to a prosthetic foot.

FIG. 2 is a view in partial section taken generally along line 2—2 of FIG. 1.

FIG. 3 is a view in partial section taken generally along line 3—3 of FIG. 2.

FIG. 4 is an exploded perspective view partially broken away of a portion of the apparatus of the present invention.

FIG. 5 is a perspective view of another portion of the apparatus of the present invention.

FIG. 6 is an exploded perspective view of the apparatus of the FIG. 5.

FIG. 7 is a top plan view of a portion of the apparatus of the present invention usable with the elements of FIGS. 5 and 6.

FIG. 8 is a perspective view of an alternate embodiment of the apparatus of FIG. 5.

FIG. 9 is a top plan view of an alternate embodiment of a portion of the apparatus of the present invention usable with the embodiment of FIG. 8.

DESCRIPTION OF THE PREFERRED EMBODIMENT

FIG. 1 is a perspective view of prosthetic foot 2 to which is secured shock absorber apparatus 10 embodying the present invention. FIG. 2 is a view in partial section through the apparatus 10 taken generally along line 2—2 of FIG. 1. The foot 2 is shown, with the shock absorber apparatus 10 shown secured thereto. The foot 2 comprises the use environment of the apparatus 10. FIG. 3 is a view in partial section taken generally along line 3—3 of FIG. 2, illustrating the securing of the apparatus 10 to the prosthetic foot 2.

The prosthetic shock absorber apparatus 10 includes an outer cylindrical element 12 which is secured directly to the prosthetic foot 2. A tubular member 40 extends inside the cylindrical element 12 and moves relative thereto on a sleeve 50 to absorb the shock of movement of the user to whom the foot 2 and the apparatus 10 is secured. The upper portion of the tubular member 40 will be appropriately secured to the user of the apparatus. If desired, of course, the apparatus 10 may be inverted, with the tubular member 40 secured to the foot 2 and the cylindrical member 12 secured to a knee joint, etc.

A sleeve 50 is disposed within the tubular member 40 and moves therewith in a longitudinal or axial movement. A bushing 70 is secured to the tubular member 40 and moves therewith and within the outer cylindrical element 12. The bushing 70 and the sleeve 50 are functionally secured together. Within the sleeve 50 is a spring steel element 100 and a flexure or shock absorbing assembly which includes three elastomeric elements 102, 106, and 110. FIG. 5 is a perspective view of the assembled element 100 and the three elements 102, 106, and 110. FIG. 6 is an exploded perspective view of the elements shown in FIG. 5.

For the following discussion, reference will be made to FIGS. 1, 2, 3, 4, 5, and 6. A particular figure will be specifically referenced as appropriate.

The outer cylindrical element 12 comprises a cylinder divided into two general portions, including a socket or connector portion 14 which terminates in an inwardly tapering end 16. A socket 18 extends upwardly and inwardly from the end 16. Four threaded apertures 20 extend through the connector portion 14 and receive threaded set screws 22 to secure the apparatus 10 to the foot 2. The foot 2 includes a generally convex connector element 4 which extends into the socket 18. The connector element 4 includes recessed connector flats 6 against which the set screws 22 bear to secure the apparatus 10 to the foot 2.

The portion of the element 12 above the socket portion receives the sleeve 50. A wall 24 comprises the upper portion of the socket 18 and the bottom end wall of the upper portion of the cylinder 12 which includes a bore 30. A slot 26 extends through the wall 24 and receives the bottom portion of the element 100. At the top of the cylinder 12 are external threads 28. The threads 28 are used to secure a cap 80 to the cylinder 12.

The tubular member 40 includes a lower end 42 which is disposed in the bore 30. Within the tubular member 40 is a bore 44. The sleeve 50 is disposed in the bore 44. FIG. 4 includes a perspective view of the sleeve 50, and FIG. 7 comprises a top plan view of the sleeve 50. Reference will be made to those figures, as well as to FIG. 2, for the following discussion of the sleeve 50.

The sleeve 50 is a cylindrical element which includes an upper end wall 52 through which extends a slot 54. The slot 54 is generally parallel to the slot 26 in the wall 24 and receives the opposite end of the element 100 from the end which is disposed in the slot 26. This is best shown in FIG. 2. The sleeve 50 also includes a radially outwardly extending rim 58 remote form the end wall 52.

The bushing 70 includes an upper rim 72 which extends radially outwardly and a lower rim 74 which extends radially inwardly. The bushing is generally cylindrical in configuration between the two rims 72 and 74. The upper portion of the bushing 70 is appropriately secured to the tubular member 40, as by epoxy, or the like. The securing location is identified by reference numeral 76 in FIG. 2.

The lower or bottom flange or rim 74 of the bushing 70 extends radially inwardly at the bottom of the tubular member 40 and is disposed on the radially outwardly extending flange or rim 58 of the sleeve 50. Thus, the tubular member 40, the sleeve 50, and the bushing 70 are secured together and move jointly.

The element 100 is preferably a spring steel plate which extends through the three flexure elements 102, 106, and 110. The elements 100, 102, 106, and 1 10 are cylindrical elements and are best shown in FIGS. 5 and 6. The element 102 includes a slot 104 which extends longitudinally and axially through the element and through which the plate 100 extends. The element 106 includes a slot 108, and the element 110 includes a slot 112. The three elements 102, 106, and 110 are preferably elastomeric elements which provide the shock absorbing function for the apparatus 10.

For purposes of illustration, three shock absorbing elements are shown, but fewer or more may be used, as desired. The elements may be identical in capability and size or they may very. That is, there may only be a single element, or several elements. The elements(s) may vary in shock absorbing capabilities or may be uniform in shock absorbing capabilities, as desired.

The plate 100 extends through the three elements 102, 106, and 110, and the opposite ends of the plate 100 extend into the slots 26 and 54, as shown in FIG. 2.

FIG. 7 comprises a top view of the sleeve 50, showing specifically the end wall 52 and the slot 54 which receives one end of the plate 100.

With the plate 100 fabricated of spring steel, there will be a limited rotational flexure in the element 100 which will allow a limited degree of rotational movement, not unlike a limited angular ankle movement, as the user walks and turns.

The cap 80 includes an end wall 82 and an opening 84 extends through the end wall. In actuality, the end wall may simply be considered as an inwardly extending rim through which the tubular member 40 extends and against which the upper rim 72 of the bushing 70 bears. Extending downwardly from the rim 82 is a cylindrical portion 86 which defines a bore 88. At the lower portion of the bore 88 are internal threads 90 which matingly engage the external threads 28 of the element 12.

Extending through the threads 90 are radially extending threaded apertures 92. Set screws 94 are disposed in the apertures 92 to secure the cap 90 to the member 12.

With the threads 28 and 90 extending longitudinally for a reasonable distance, the cap 80 may be used to locate the bushing 70 and the sleeve 50 relative to the members 12 and 40. Since the lengths of the members 12 and 40 are fixed, the overall length of the apparatus 10 may be adjusted by the engagement of the threads 28 and 90. Moreover, the loading, or preloading, of the flexure members 102, 106, and 110 may be adjusted by the threaded engagement.

The outer ends of the spring steel plate or member 100 extends through the slots 26 and 54 in the end wall 24 and the end wall 52, respectively, thus confining the flexure members 102, 106, and 110 between the respective end walls. The shock absorbing function is accomplished as the members 102, 106, and 110 contract or flex downwardly in response to walking movements. A limited twisting movement of the spring steel also allows a limited relative rotation of the foot 2 relative to the tubular member 40.

An alternate embodiment of the plate 100 is illustrated in FIGS. 8 and 9. FIG. 8 is a perspective view of a square rod 120 extending through three flexure members 122, 126, and 130. FIG. 9 is a top view of the sleeve 50 in an alternate configuration with a square hole or aperture 56 extending through the end wall 52. The square hole or aperture 56 receives the upper end of the square rod 120, while a similar square hole (not shown) in the wall 24 receives the bottom end of the rod 120.

The difference between the plate 100 and the rod 120 is that the rod 120 will not rotationally flex, while the plate 100 will rotationally flex, as discussed above. Accordingly, the embodiment of FIGS. 8 and 9 will not allow or provide for any rotational movement of the apparatus 10 relative to the foot 2.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, within the limits only of the true spirit and scope of the invention.

What I claim is:

1. Prosthetic apparatus comprising in combination:
    a cylindrical element, including
        a socket portion for receiving a prosthetic connector element,
        an end wall at the socket portion,
        a first slot in the end wall,
        a first bore extending from the end wall, and
        external threads remote from the end wall;
    a tubular member, including
        a first portion extending into the bore of the cylindrical element, and
        a second bore;
    a sleeve disposed in the second bore, including
        an end wall spaced apart from the end wall of the cylindrical element, a second slot in the end wall generally parallel to the slot in the end wall of the cylindrical element, and a radially outwardly extending flange remote from the end wall;

a cylindrical bushing disposed in the first bore and secured to the tubular member, including a radially inwardly extending flange disposed on the radially outwardly extending flange of the sleeve for providing joint movement of the tubular member, the sleeve, and the bushing;

means for absorbing shocks disposed in the sleeve between the end walls; and cap means secured to the external threads of the cylindrical element for securing the tubular member, the sleeve and the bushing to the cylindrical element.

2. The apparatus of claim 1 in which the means for absorbing shocks includes a flexible element.

3. The apparatus of claim 2 in which the means for absorbing shocks further includes an element extending through the flexible element and into the first and second slots.

4. The apparatus of claim 3 in which the element comprises a spring plate for providing relative rotation between the cylindrical element and the tubular member.

5. The apparatus of claim 3 in which the element comprises a rod for preventing relative rotation between the cylindrical element and the tubular member.

6. The apparatus of claim 1 in which the means for absorbing shocks includes a plurality of flexible elements.

7. The apparatus of claim 6 in which the means for absorbing shocks are elastomeric elements.

* * * * *